United States Patent
Black et al.

(10) Patent No.: US 11,612,409 B2
(45) Date of Patent: Mar. 28, 2023

(54) ULTRASONIC TRANSDUCER ALIGNMENT OF AN ARTICULATING ULTRASONIC SURGICAL INSTRUMENT

(71) Applicant: Ethicon LLC, Guaynabo, PR (US)

(72) Inventors: Brian D. Black, Loveland, OH (US); Morgan R. Hunter, Cincinnati, OH (US); Karl W. Mueller, Loveland, OH (US)

(73) Assignee: Cilag GmbH International, Zug (CH)

( * ) Notice: Subject to any disclaimer, the term of this patent is extended or adjusted under 35 U.S.C. 154(b) by 412 days.

(21) Appl. No.: 16/556,667

(22) Filed: Aug. 30, 2019

(65) Prior Publication Data

US 2021/0059710 A1 Mar. 4, 2021

(51) Int. Cl.
*A61B 17/32* (2006.01)
*A61B 17/295* (2006.01)
*A61B 17/29* (2006.01)

(52) U.S. Cl.
CPC .... *A61B 17/320092* (2013.01); *A61B 17/295* (2013.01); *A61B 2017/2903* (2013.01); *A61B 2017/2947* (2013.01); *A61B 2017/320071* (2017.08); *A61B 2017/320094* (2017.08)

(58) Field of Classification Search
CPC .... A61B 17/320092; A61B 2017/2925; A61B 2017/320093; A61B 2017/00429; A61B 2017/320094; A61B 2017/00424; A61B 2017/320095; A61B 2017/2929
See application file for complete search history.

(56) References Cited

U.S. PATENT DOCUMENTS

| | | | |
|---|---|---|---|
| 5,322,055 A | 6/1994 | Davison et al. |
| 5,873,873 A | 2/1999 | Smith et al. |
| 5,980,510 A | 11/1999 | Tsonton et al. |
| 6,063,098 A | 5/2000 | Houser et al. |
| 6,325,811 B1 | 12/2001 | Messerly |
| 6,500,176 B1 | 12/2002 | Truckai et al. |
| 6,773,444 B2 | 8/2004 | Messerly |
| 6,783,524 B2 | 8/2004 | Anderson et al. |
| 7,112,201 B2 | 9/2006 | Truckai et al. |

(Continued)

OTHER PUBLICATIONS

U.S. Appl. No. 16/556,625, entitled "Ultrasonic Surgical Instrument with Axisymmetric Clamping," filed Aug. 30, 2019.

(Continued)

*Primary Examiner* — Ashley L Fishback
(74) *Attorney, Agent, or Firm* — Frost Brown Todd LLP

(57) ABSTRACT

An ultrasonic surgical instrument and method of deflecting an end effector includes the end effector having an ultrasonic blade, a shaft assembly defining a longitudinal axis, and a body assembly. The shaft assembly has an articulation section configured to articulate from a straight configuration to an articulated configuration and an acoustic waveguide with a flexible waveguide portion positioned within the articulation section. The body assembly proximally extends from the shaft assembly and includes a housing and a shiftable transducer. The shiftable transducer is secured to the acoustic waveguide and configured to generate an ultrasonic energy. In addition, the shiftable transducer assembly is movably mounted relative to the housing and configured to accommodate deflection of the end effector.

18 Claims, 10 Drawing Sheets

(56) References Cited

U.S. PATENT DOCUMENTS

| | | | |
|---|---|---|---|
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 8,461,744 B2 * | 6/2013 | Wiener | A61B 18/18 606/171 |
| 8,479,969 B2 | 7/2013 | Shelton, IV |
| 8,573,461 B2 | 11/2013 | Shelton, IV et al. |
| 8,573,465 B2 | 11/2013 | Shelton, IV |
| 8,591,536 B2 | 11/2013 | Robertson |
| 8,602,288 B2 | 12/2013 | Shelton, IV et al. |
| 8,616,431 B2 | 12/2013 | Timm et al. |
| 8,623,027 B2 | 1/2014 | Price et al. |
| 8,663,220 B2 | 3/2014 | Wiener et al. |
| 8,783,541 B2 | 7/2014 | Shelton, IV et al. |
| 8,800,838 B2 | 8/2014 | Shelton, IV |
| 8,820,605 B2 | 9/2014 | Shelton, IV |
| 8,844,789 B2 | 9/2014 | Shelton, IV et al. |
| 8,911,460 B2 | 12/2014 | Neurohr et al. |
| 9,023,071 B2 | 5/2015 | Miller et al. |
| 9,095,367 B2 | 8/2015 | Olson et al. |
| 9,301,759 B2 | 4/2016 | Spivey et al. |
| 9,381,058 B2 | 7/2016 | Houser et al. |
| 9,393,037 B2 | 7/2016 | Olson et al. |
| 9,402,682 B2 | 8/2016 | Worrell et al. |
| 9,949,785 B2 | 4/2018 | Price et al. |
| 10,034,683 B2 | 7/2018 | Monroe et al. |
| 10,172,636 B2 | 1/2019 | Stulen et al. |
| 10,226,274 B2 | 3/2019 | Worrell et al. |
| 10,342,567 B2 | 7/2019 | Hibner et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2011/0087212 A1 | 4/2011 | Aldridge et al. |
| 2012/0116265 A1 | 5/2012 | Houser et al. |
| 2014/0005681 A1 | 1/2014 | Gee et al. |
| 2014/0005702 A1 | 1/2014 | Timm et al. |
| 2015/0320438 A1 | 11/2015 | Weisenburgh, II et al. |
| 2016/0015419 A1 * | 1/2016 | Hibner | A61B 18/1482 606/171 |
| 2016/0302818 A1 | 10/2016 | Weisenburgh, II et al. |
| 2016/0302819 A1 | 10/2016 | Stulen et al. |
| 2017/0105757 A1 | 4/2017 | Weir et al. |
| 2017/0135718 A1 * | 5/2017 | Lyons | A61B 17/295 |
| 2017/0202591 A1 * | 7/2017 | Shelton, IV | A61B 18/00 |
| 2017/0281217 A1 | 10/2017 | Hibner |
| 2017/0281218 A1 | 10/2017 | Timm |
| 2017/0281219 A1 | 10/2017 | Hibner et al. |
| 2017/0281220 A1 | 10/2017 | Hibner et al. |
| 2017/0281221 A1 | 10/2017 | Boudreaux |
| 2019/0059931 A1 | 2/2019 | Shelton, IV et al. |
| 2019/0059933 A1 * | 2/2019 | Miller | A61B 17/320068 |

OTHER PUBLICATIONS

U.S. Appl. No. 16/556,635, entitled "Ultrasonic Blade and Clamp Arm Alignment Features," filed Aug. 30, 2019.

U.S. Appl. No. 16/556,661, entitled "Ultrasonic Surgical Instrument with a Multi-Planar Articulating Shaft Assembly," filed Aug. 30, 2019.

U.S. Appl. No. 16/556,727, entitled "Rotatable Linear Actuation Mechanism," filed Aug. 30, 2019.

U.S. Appl. No. 61/410,603, entitled "Energy-Based Surgical Instruments," filed Nov. 5, 2010.

International Search Report and Written Opinion dated Dec. 14, 2020, for International Application No. PCT/IB2020/057737, 16 pages.

European Search Report and Written Opinion dated Jan. 18, 2023 for Application No. EP 22202107.3, 10 pgs.

* cited by examiner

ULTRASONIC TRANSDUCER ALIGNMENT OF AN ARTICULATING ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Such surgical instruments may be directly gripped and manipulated by a surgeon or incorporated into a robotically assisted surgery. During robotically assisted surgery, the surgeon typically operates a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller typically includes one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a tissue grasper, a needle driver, an electrosurgical cautery probes, etc. Each of these structures performs functions for the surgeon, for example, cutting tissue, coagulating tissue, holding or driving a needle, grasping a blood vessel, dissecting tissue, or cauterizing tissue.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pat. No. 9,023,071, entitled "Ultrasonic Device for Fingertip Control," issued May 5, 2015, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. patent application Ser. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; U.S. Pat. No. 9,095,367, issued Aug. 4, 2015, entitled "Flexible Harmonic Waveguides/Blades for Surgical Instruments," the disclosure of which is incorporated by reference herein; U.S. Pat. No. 10,226,274, issued Mar. 12, 2019, entitled "Ultrasonic Surgical Instrument with Articulation Joint Having Plurality of Locking Positions," the disclosure of which is incorporated by reference herein; U.S. Pat. No. 10,034,683, entitled "Ultrasonic Surgical Instrument with Rigidizing Articulation Drive Members," issued Jul. 31, 2018, the disclosure of which is incorporated by reference herein; U.S. Pat. Pub. No. 2016/0302818, published Oct. 10, 2016, now abandoned, entitled "Ultrasonic Surgical Instrument with Movable Rigidizing Member," the disclosure of which is incorporated by reference herein, now abandoned; U.S. Pat. Pub. No. 2016/0302819, published Oct. 20, 2016, now abandoned, entitled "Ultrasonic Surgical Instrument with Articulating End Effector having a Curved Blade," the disclosure of which is incorporated by reference herein, now abandoned; U.S. Pat. No. 10,342,567, issued Jul. 9, 2019, entitled "Ultrasonic Surgical Instrument with Opposing Thread Drive for End Effector Articulation," the disclosure of which is incorporated by reference herein; U.S. Pat. Pub. No. 2015/0320438, published Nov. 12, 2015, issued as U.S. Pat. No. 10,667,835 on Jun. 2, 2020, entitled "Ultrasonic Surgical Instrument with End Effector Having Restricted Articulation," the disclosure of which is incorporated by reference herein; U.S. Pat. Pub. No. 2017/0281217, published Oct. 5, 2017, issued as U.S. Pat. No. 10,492,819 on Dec. 3, 2019, entitled "Surgical Instrument with Dual Mode Articulation Drive," the disclosure of which is incorporated by reference herein; U.S. Pat. Pub. No. 2017/0281218, published Oct. 5, 2017, issued as U.S. Pat. No. 10,507,034 on Dec. 17, 2019, entitled "Surgical Instrument with Motorized Articulation Drive in Shaft Rotation Knob," the disclosure of which is incorporated by reference herein; U.S. Pat. Pub. No. 2017/0281219, published Oct. 5, 2017, issued as U.S. Pat. No. 10,743,850 on Aug. 18, 2020, entitled "Surgical Instrument with Locking Articulation Drive Wheel," the disclosure of which is incorporated by reference herein; U.S. Pat. Pub. No. 2017/0281220, published Oct. 5, 2017, issued as U.S. Pat. No. 10,575,836 on Mar. 3, 2020, entitled "Surgical Instrument with Selectively Locked Articulation Assembly," the disclosure of which is incorporated by reference herein; and U.S. Pat. Pub. No. 2017/0281221, published Oct. 5, 2017, issued as U.S. Pat. No. 10,405,876 on Sep. 10, 2019, entitled "Articulation Joint for Surgical Instrument," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein; and U.S. Pat. No. 8,663,220, entitled "Ultrasonic Surgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
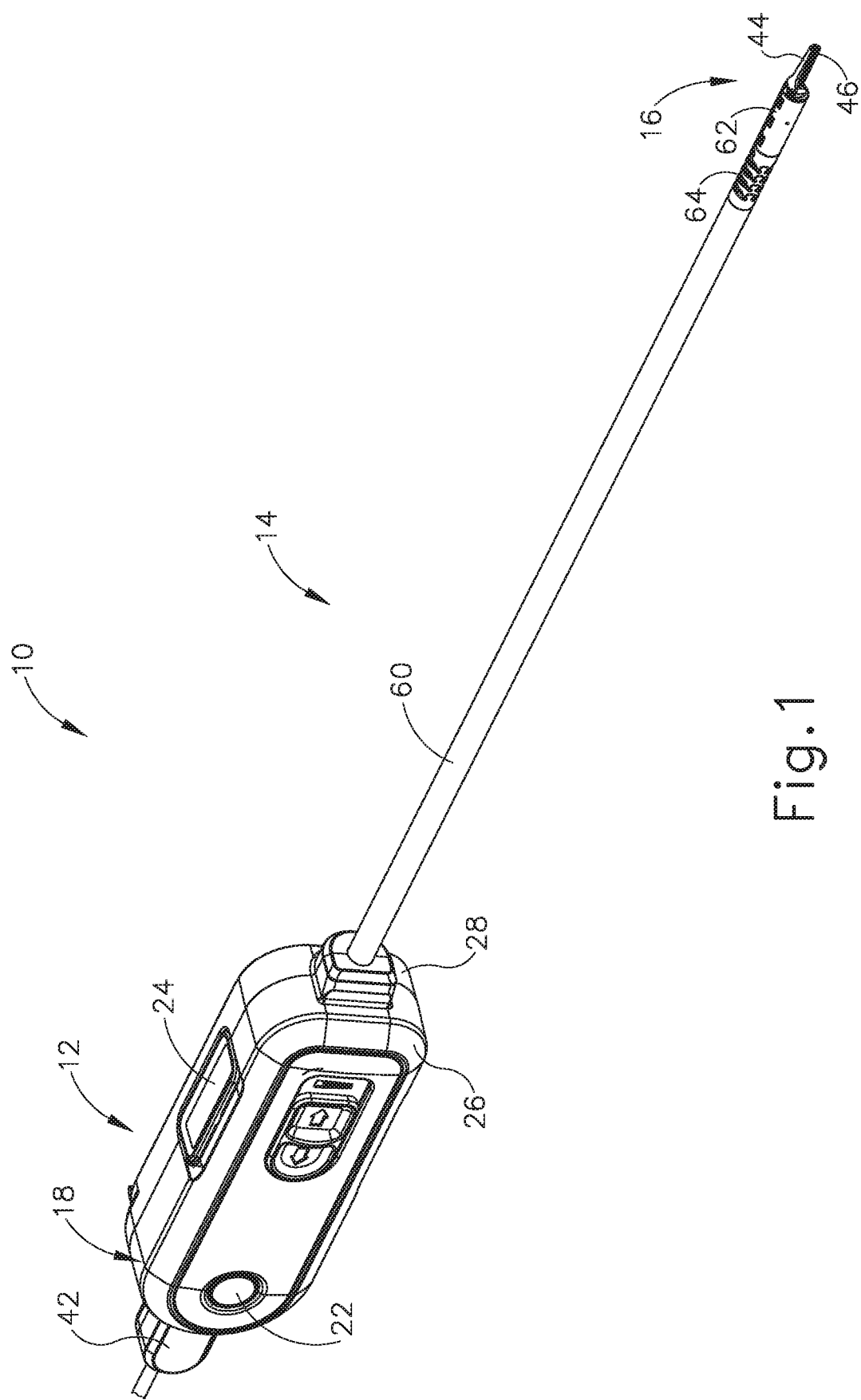
FIG. 1 depicts a front perspective view of a first example of an ultrasonic surgical instrument having an end effector, a first exemplary shaft assembly, and a first exemplary base assembly configured to connect to a robotic driven interface.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "rear," "clockwise," "counterclockwise," "longitudinal," and "transverse" also are used herein for reference to relative positions and directions. Such terms are used below with reference to views as illustrated for clarity and are not intended to limit the invention described herein.

I. Exemplary Surgical Instrument

FIG. 1 shows an exemplary surgical instrument, such as an ultrasonic surgical instrument (10). At least part of ultrasonic surgical instrument (10) may be constructed and operable in accordance with at least some of the teachings of any of the various patents, patent application publications, and patent applications that are cited herein. As described therein and as will be described in greater detail below, ultrasonic surgical instrument (10) is operable to cut tissue and seal or weld tissue (e.g., a blood vessel, etc.) substantially simultaneously. While the present example incorporates various ultrasonic features as ultrasonic surgical instrument (10), the invention is not intended to be unnecessarily limited to the ultrasonic features described herein.

Ultrasonic surgical instrument (10) of the present example comprises a body assembly, such as a base assembly (12), a shaft assembly (14), and an end effector (16). Base assembly (12) includes a housing (18), a button (22), and a pair of latch clasps (24). Button (22) is operatively connected to an electrical base power controller (not shown) and configured to selectively power ultrasonic surgical instrument (10) for use. In addition, housing (18) of the present example includes a front housing cover (26) and a rear housing cover (28) removably secured together via latch clasps (24). More particularly, latch clasps (24) removably secure front housing cover (26) to rear housing cover (28) such that front housing cover (26) may be removed for accessing an interior space (30) (see FIG. 5) within base assembly (12). Shaft assembly (14) distally extends from base assembly (12) to end effector (16) to thereby communicate mechanical and/or electrical forces therebetween for use as will be discussed below in greater detail. As shown in the present example, base assembly (12) is configured to operatively connect to a robotic drive (not shown) for driving various features of shaft assembly (14) and/or end effector (16). However, in another example, body assembly may alternatively include a handle assembly (not shown), which may include a pistol grip (not shown) in one example, configured to be directly gripped and manipulated by the surgeon for driving various features of shaft assembly (14) and/or end effector (16). The invention is thus not intended to be unnecessarily limited to use with base assembly (12) and the robotic drive (not shown).

Figure 2:
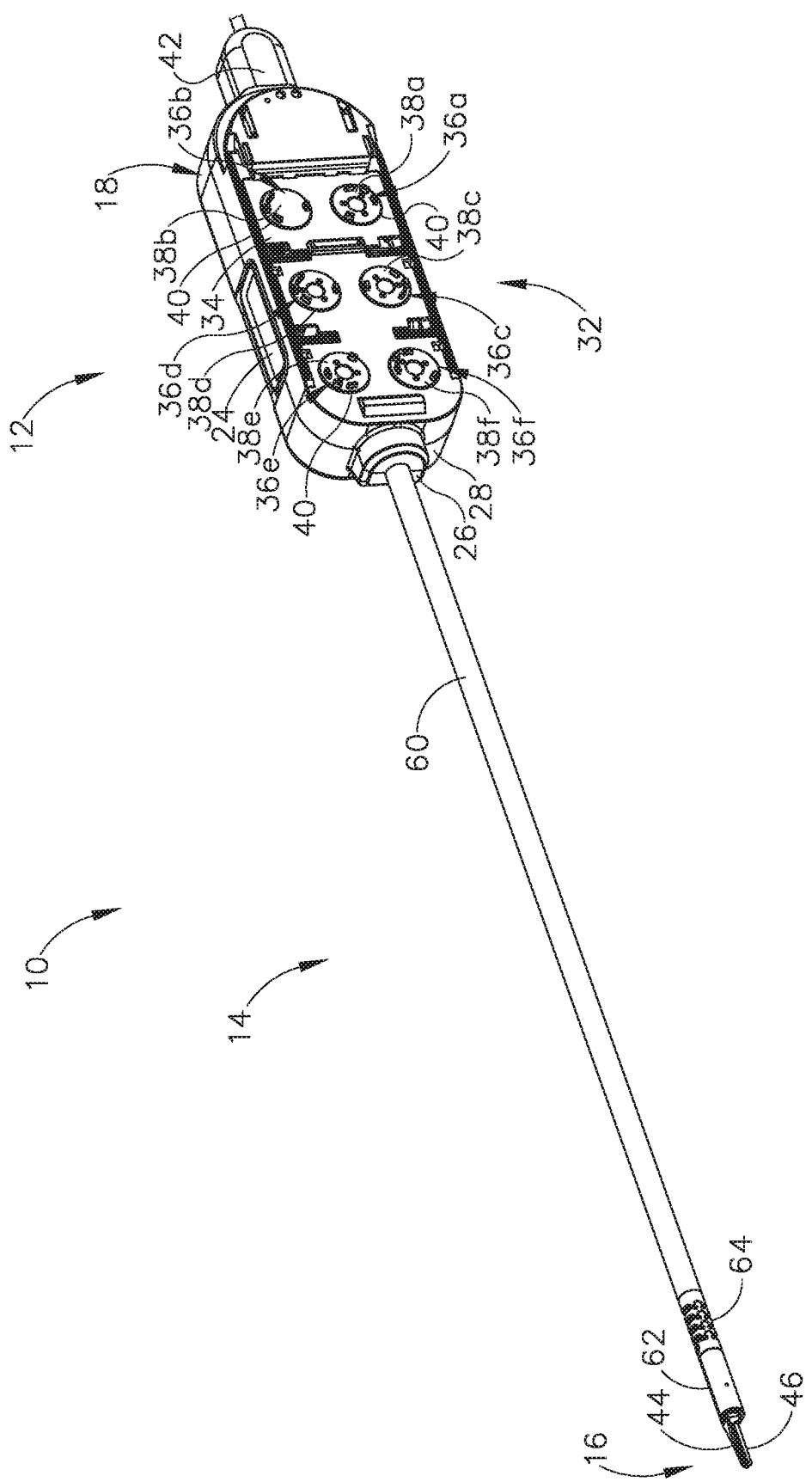
FIG. 2 depicts a rear perspective view of the ultrasonic surgical instrument of FIG. 1.

To this end, with respect to FIG. 2, base assembly (12) includes a robotic driven interface (32) extending through a base plate (34) of rear housing cover (28) and configured to mechanically couple with the robotic drive (not shown). Robotic driven interface (32) of the present example includes a plurality of instrument actuators (36a, 36b, 36c, 36d, 36e, 36f) having a plurality of input bodies (38a, 38b, 38c, 38d, 38e, 38f), respectively. Each input body (38a, 38b, 38c, 38d, 38e, 38f), which may also be referred to herein as a "puck," is configured to removably connect with the robotic drive (not shown) and, in the present example, is generally cylindrical and rotatable about an axis. Input bodies (38a, 38b, 38c, 38d, 38e, 38f) have a plurality of slots (40) configured to receive portions of the robotic drive (not shown) for gripping and rotatably driving input bodies (38a, 38b, 38c, 38d, 38e, 38f) in order to direct operation of shaft assembly (14) and/or end effector (16) as will be discussed below in greater detail. Base assembly (12) also receives an electrical plug (42) operatively connected to an electrical power source (not shown) to provide electrical power to base assembly (12) for operation as desired, such as powering electrical base power controller (not shown) and directing electrical energy to various features of shaft assembly (14) or end effector (16) associated with cutting, sealing, or welding tissue.

A. Exemplary End Effector and Acoustic Drivetrain

Figure 3A:
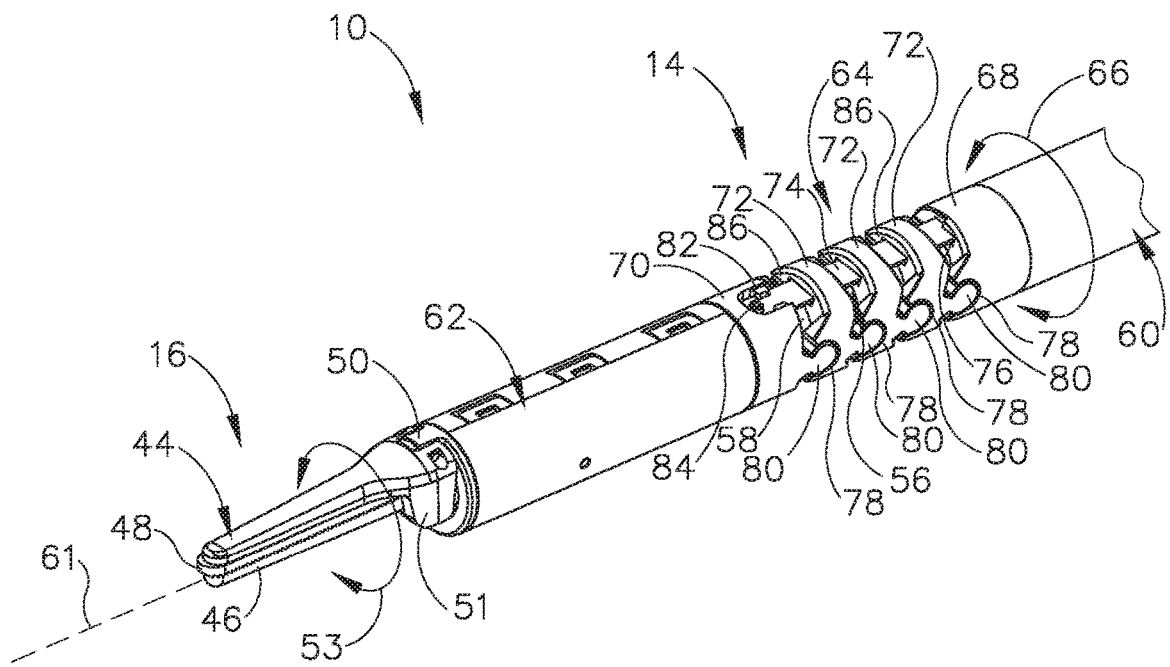
FIG. 3A depicts an enlarged perspective view of the ultrasonic surgical instrument of FIG. 1 with the end effector in a closed position and the shaft assembly in a straight configuration.
Figure 3B:
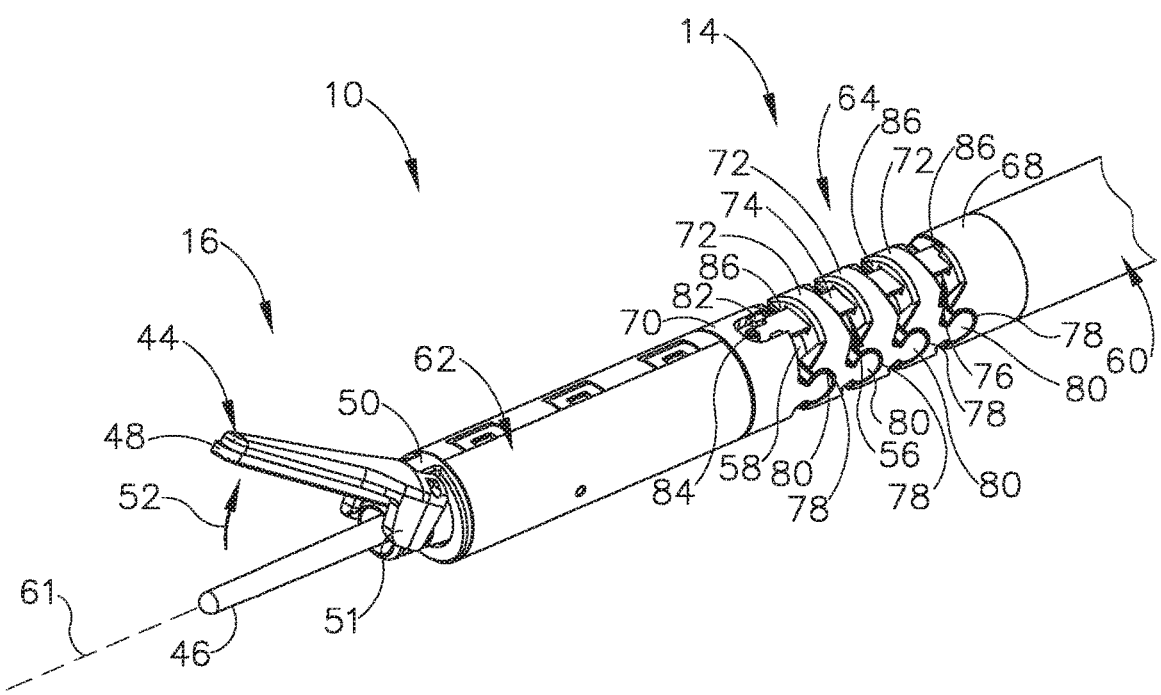
FIG. 3B depicts the enlarged perspective view of the ultrasonic surgical instrument similar to FIG. 3A, but showing the end effector in an open position.

As best seen in FIGS. 3A-3B, end effector (16) of the present example includes a clamp arm (44) and an ultrasonic blade (46). Clamp arm (44) has a clamp pad (48) secured to an underside of clamp arm (44), facing blade (46). In one example, clamp pad (48) may comprise polytetrafluoroethylene (PTFE) and/or any other suitable material(s). Clamp arm (44) is pivotally secured to a distally projecting tongue (50) of shaft assembly (14). Clamp arm (44) is operable to selectively pivot toward and away from blade (46) to selectively clamp tissue between clamp arm (44) and blade (46). A pair of arms (51) extend transversely from clamp arm (44) and are pivotally secured to another portion of shaft assembly (14) configured to longitudinally slide to pivot clamp arm (44) as indicated by an arrow (52) between a closed position shown in FIG. 3A and an open position shown in FIG. 3B.

In addition to pivoting relative to blade (46), clamp arm (44) of the present example is further configured to rotate about blade (46) relative to blade (46) and also relative to shaft assembly (14) as indicated by an arrow (53). In one example, clamp arm (44) rotates in the clockwise or counterclockwise directions completely around blade (46) and may be selectively fixed in any angular position relative to blade (46) for directing clamp arm (44) from the open position to the closed position for clamping tissue. In another example, clamp arm (44) may have rotational stops (not shown) configured to limit rotational movement of clamp arm (44) relative to blade (46) in one or more predetermined positions.

Blade (46) of the present example is operable to vibrate at ultrasonic frequencies in order to effectively cut through and seal tissue, particularly when the tissue is being compressed between clamp pad (48) and blade (46). Blade (46) is positioned at a distal end of an acoustic drivetrain. This acoustic drivetrain includes a transducer assembly (54) (see FIG. 5) and an acoustic waveguide (56), which includes a flexible portion (58) discussed below in greater detail. It should be understood that waveguide (56) may be configured to amplify mechanical vibrations transmitted through waveguide (56). Furthermore, waveguide (56) may include features operable to control the gain of the longitudinal vibrations along waveguide (56) and/or features to tune waveguide (56) to the resonant frequency of the system. Various suitable ways in which waveguide (56) may be mechanically and acoustically coupled with transducer assembly (54) (see FIG. 5) will be apparent to those of ordinary skill in the art in view of the teachings herein.

Those of ordinary skill in the art will understand that, as a matter of physics, a distal end of blade (46) is located at a position corresponding to an anti-node associated with resonant ultrasonic vibrations communicated through flexible portion (58) of waveguide (56). When transducer assembly (54) (see FIG. 5) is energized, the distal end of blade (46) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (54) (see FIG. 5) of the present example is activated, these mechanical oscillations are transmitted through waveguide (56) to reach blade (46), thereby providing oscillation of blade (46) at the resonant ultrasonic frequency. Thus, when tissue is secured between blade (46) and clamp pad (48), the ultrasonic oscillation of blade (46) may simultaneously sever the tissue and denature the proteins in adjacent tissue cells, thereby providing a coagulative effect with relatively little thermal spread. In some versions, end effector (16) is operable to apply radiofrequency (RF) electrosurgical energy to tissue in addition to applying ultrasonic energy to tissue. In any case, other suitable configurations for an acoustic transmission assembly and transducer assembly (54) will be apparent to one of ordinary skill in the art in view of the teachings herein. Similarly, other suitable configurations for end effector (16) will be apparent to those of ordinary skill in the art in view of the teachings herein.

B. Exemplary Shaft Assembly and Articulation Section

As shown in FIGS. 3A-3B, shaft assembly (14) includes a proximal shaft portion (60) extending along a longitudinal axis (61), a distal shaft portion (62) distally projecting relative to the proximal shaft portion (60), and an articulation section (64) extending between proximal and distal shaft portions (60, 62). Shaft assembly (14) is configured to rotate about longitudinal axis (61) as indicated by an arrow (66). In one example, shaft assembly (14) rotates in the clockwise or counterclockwise directions completely around longitudinal axis (61) and may be selectively fixed in any rotational position about longitudinal axis (61) for positioning articulation section (64) and/or end effector (16) about longitudinal axis (61). While end effector (16) generally rotates with shaft assembly (14) as indicated by arrow (66), end effector (16) may be simultaneously and independently rotated as indicated by arrow (53) relative to shaft assembly (14) during use for repositioning portions of shaft assembly (14) and/or end effector (16) as desired.

Articulation section (64) is configured to selectively position end effector (16) at various lateral deflection angles relative to longitudinal axis (61) defined by proximal shaft portion (60). Articulation section (64) may take a variety of forms. In the present example, articulation section (64) includes a proximal link (68), a distal link (70), and a plurality of intermediate links (72) connected in series between proximal and distal links (68, 70). Articulation section (64) further includes a pair of articulation bands (74) extending along a pair of respective channels (76) collectively defined through links (68, 70, 72). Links (68, 70, 72) are generally configured to pivot relative to each other upon actuation of articulation bands (74) to thereby bend articulation section (64) with flexible portion (58) of waveguide (56) therein to achieve an articulated state. By way of example only, articulation section (64) may alternatively or additionally be configured in accordance with one or more teachings of U.S. Pat. No. 9,402,682, entitled "Articulation Joint Features for Articulating Surgical Device," issued Aug. 2, 2016, the disclosure of which is incorporated by reference herein. As another merely illustrative example, articulation section (64) may alternatively or additionally be configured in accordance with one or more teachings of U.S. Pat. No. 9,393,037, issued Jul. 19, 2016, entitled "Surgical Instruments with Articulating Shafts," the disclosure of which is incorporated by reference herein and U.S. Pat. No. 9,095,367, issued Aug. 4, 2015, entitled "Flexible Harmonic Waveguides/Blades for Surgical Instruments," the disclosure of which is incorporated by reference herein. In addition to or in lieu of the foregoing, articulation section (64) and/or may be constructed and/or operable in accordance with at least some of the teachings of U.S. Pat. No. 10,034,683, entitled "Ultrasonic Surgical Instrument with Rigidizing Articulation Drive Members," issued on Jul. 31, 2018. Alternatively, articulation section (64) may be constructed and/or operable in any other suitable fashion.

Links (68, 70, 72) shown in FIGS. 3B-4B pivotally interlock to secure distal shaft portion (62) relative to proximal shaft portion (60) while allowing for deflection of distal shaft portion (62) relative to longitudinal axis (61). In the present example, proximal link (68) is rigidly connected to proximal shaft portion (60) and has a pair of arcuate grooves (78) opposed from each other. Intermediate links (72) respectively have a pair of arcuate tongues (80) proximally extending therefrom and a pair of arcuate grooves (78) positioned distally opposite from respective tongues (80). Each intermediate link (72) has tongues (80) pivotally received within adjacent arcuate grooves (78) of another intermediate link (72) or proximal link (68) as applicable. Distal link (70) is rigidly connected to distal shaft portion (62) and has another pair of arcuate tongues (80) opposed from each other and pivotally received within adjacent arcuate grooves (78) of intermediate link (72). Tongues (80) and grooves (78) connect together to form the series of interlocked links (68, 70, 72).

Figure 4A:
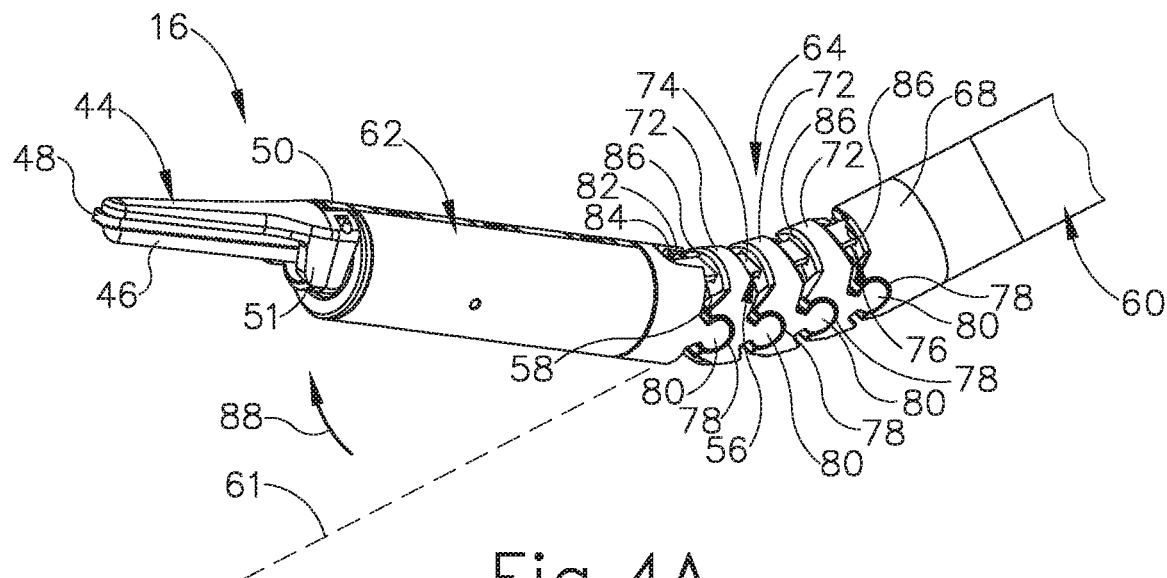
FIG. 4A depicts an enlarged perspective view of the ultrasonic surgical instrument of FIG. 1 with the end effector in a closed position and the shaft assembly in a first articulated configuration.
Figure 4B:
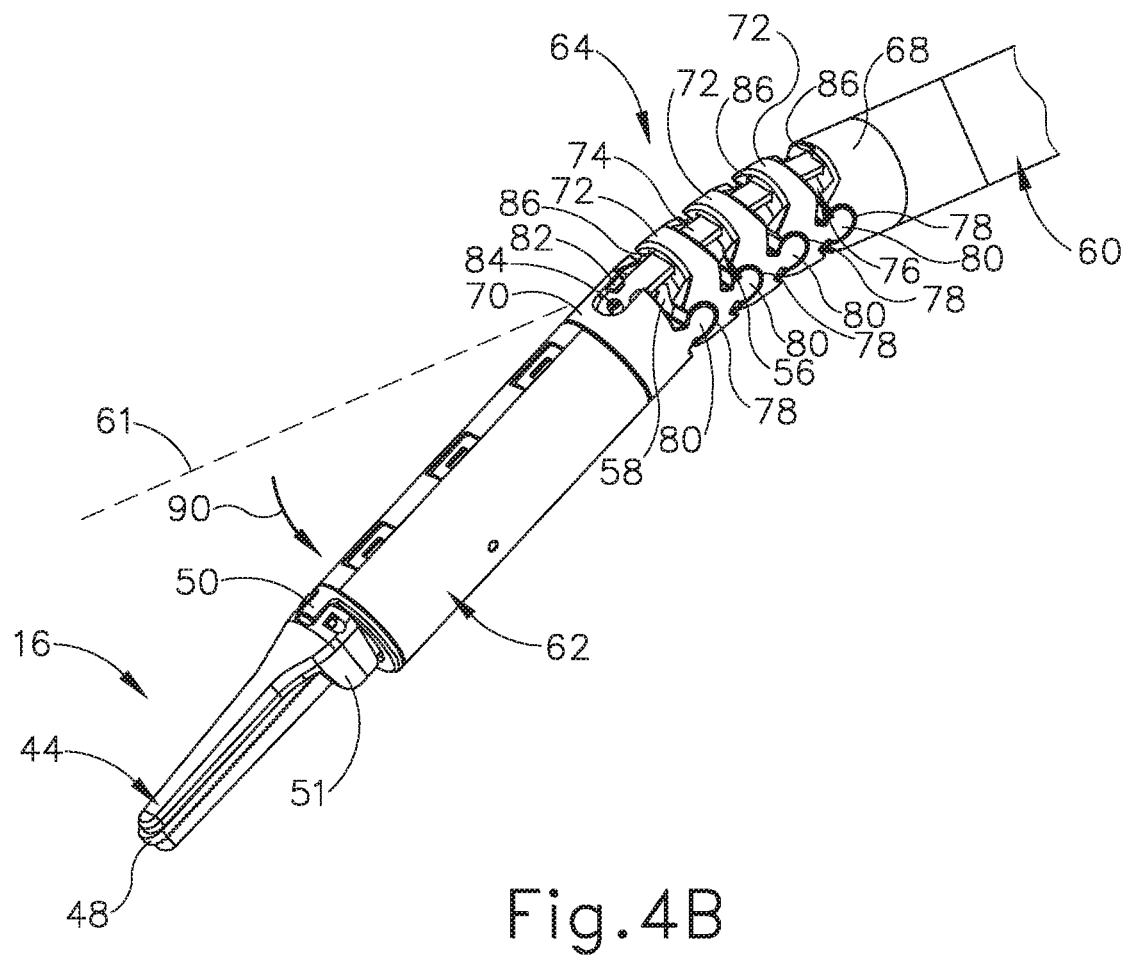
FIG. 4B depicts the enlarged perspective view of the ultrasonic surgical instrument similar to FIG. 4A, but with the shaft assembly in a second articulated configuration.

Distal link (70) further includes a pair of opposing notches (82) with a pin (84) therein configured to receive distal end portions of respective articulation bands (74). More particularly, pins (84) extend through a hole in each respective articulation bands (74) while distal end portions of respective articulation bands (74) are coupled within notches (82). Slots (86) in each of intermediate and proximal links (72, 68) longitudinally align with each other and notches (82) to collectively define channels (76) configured to receive articulation bands (74) while allowing articulation bands (74) to slide relative to links (68, 70, 72). To this end, when articulation bands (74) translate longitudinally in an opposing fashion, this will cause articulation section (64) to bend, thereby laterally deflecting end effector (16) away from the longitudinal axis (61) of proximal shaft portion (60) from a straight configuration as shown in FIG. 3B to a first articulated configuration as shown in FIG. 4A and indicated by an arrow (88) or a second articulated configuration as shown in FIG. 4B and indicated by an arrow (90). In particular, end effector (16) will be articulated toward the articulation band (74) that is being pulled proximally. During such articulation, the other articulation band (74) may be pulled distally. Alternatively, the other articulation band (74) may be driven distally by an articulation control. Furthermore, flexible acoustic waveguide (56) is configured to effectively communicate ultrasonic vibrations from waveguide (56) to blade (46) even when articulation section (64) is in an articulated configuration as shown in FIGS. 4A-4B.

C. Exemplary Base Assembly with Instrument Actuators for Robotic Interface

Figure 5:
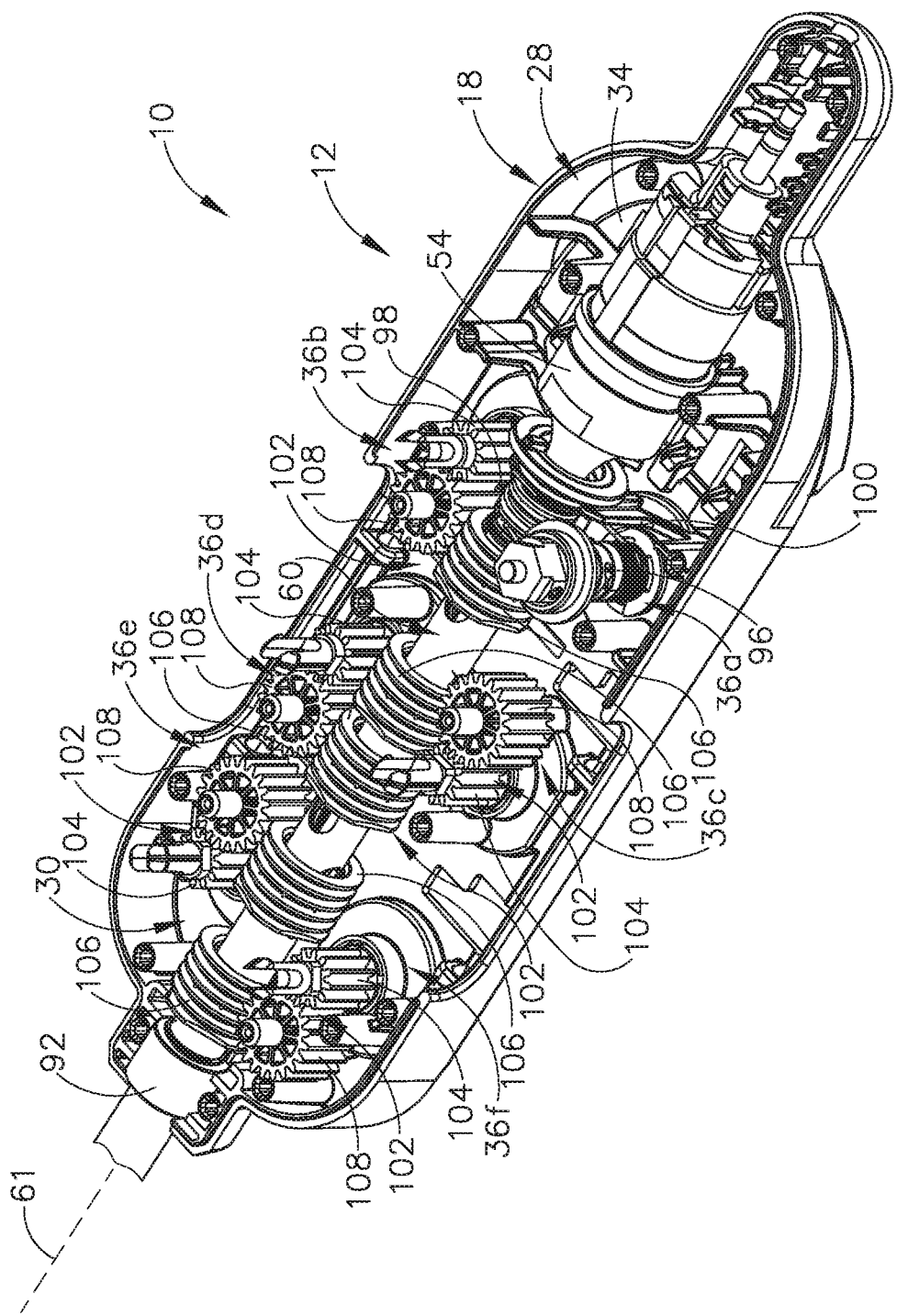
FIG. 5 depicts an enlarged perspective view of the ultrasonic surgical instrument of FIG. 1 with the base assembly having various components removed for greater clarity of an interior space of the base assembly.

FIG. 5 shows interior space (30) of base assembly (12) with instrument actuators (36a, 36b, 36c, 36d, 36e, 36f) in greater detail. Generally, instrument actuators (36a, 36b, 36c, 36d, 36e, 36f) are engaged with shaft assembly (14) and configured to direct movement of end effector (16) and/or shaft assembly (14), such as movement indicated above in one example by arrows (52, 53, 66, 88, 90) (see FIGS. 3A-4B). Shaft assembly (14) is received within base assembly (12) and supported by bearings (92) therein to operatively connect each respective instrument actuator (36a, 36b, 36c, 36d, 36e, 36f) to shaft assembly (14) as well as operatively connect acoustic waveguide (56) (see FIG. 3A) to transducer assembly (54) and a generator (not shown) of the acoustic drivetrain. More particularly, transducer assembly (54) is coupled with generator (not shown) such that transducer assembly (54) receives electrical power from generator (not shown). Piezoelectric elements (not shown) in transducer assembly (54) convert that electrical power into ultrasonic vibrations. Generator (not shown) may be coupled to the electrical power source (not shown) via electrical plug (42) (see FIG. 1) and a control module (not shown) that are configured to provide a power profile to transducer assembly (54) that is particularly suited for the generation of ultrasonic vibrations through transducer assembly (54). By way of example only, generator (not shown) may comprise a GEN04 or GENII sold by Ethicon Endo-Surgery, Inc. of Cincinnati, Ohio. In addition or in the alternative, generator (not shown) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. Still other suitable forms that generator (not shown) may take, as well as various features and operabilities that generator (not shown) may provide, will be apparent to those of ordinary skill in the art in view of the teachings herein.

Figure 6:
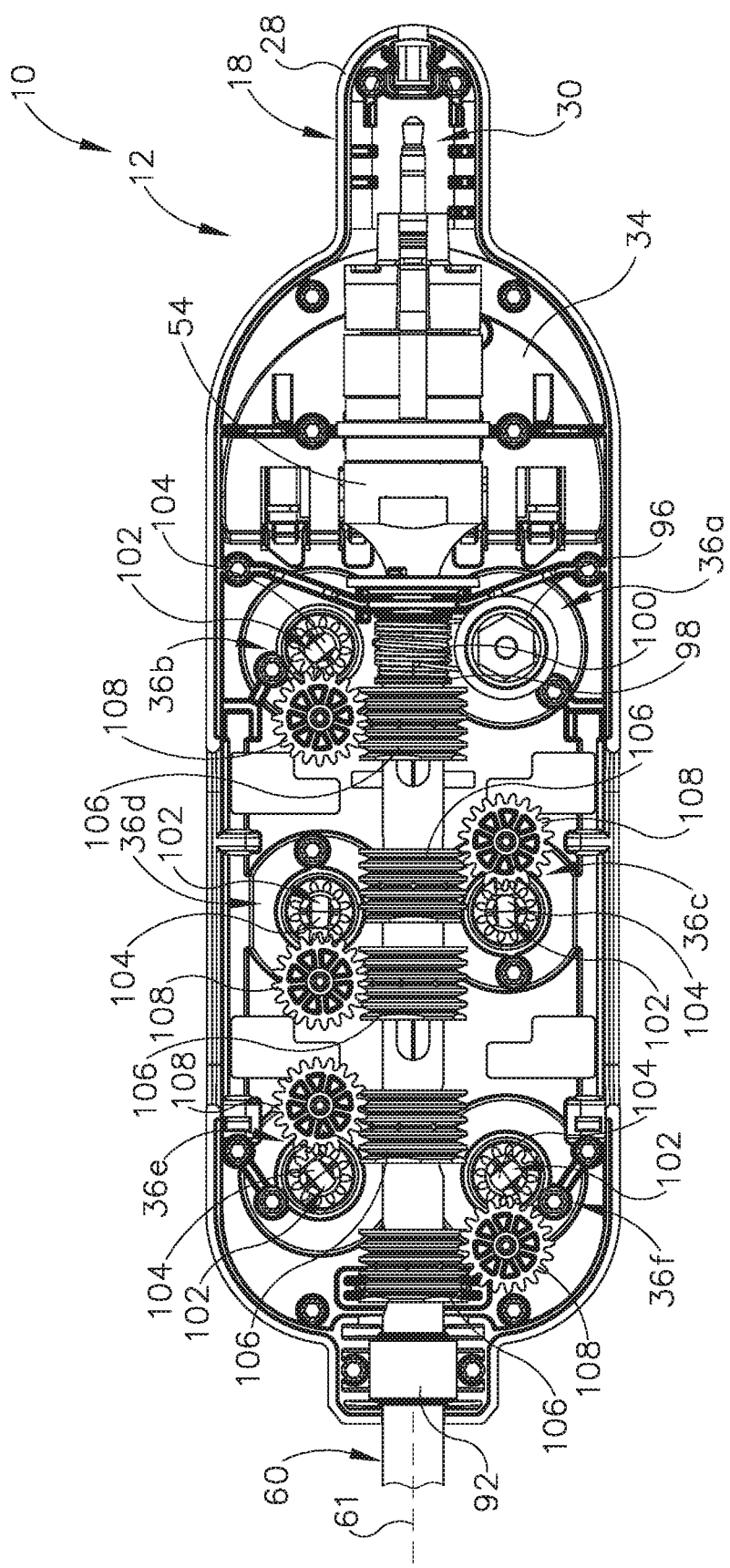
FIG. 6 depicts an enlarged front view of the ultrasonic surgical instrument of FIG. 1 with the base assembly having various components removed for greater clarity of the interior space of the base assembly.

The present example of base assembly (12) shown in FIGS. 5-6 includes six instrument actuators (36a, 36b, 36c, 36d, 36e, 360, although it will be appreciated that any such number of such instrument actuators (36a, 36b, 36c, 36d, 36e, 360 configured to direct movement of shaft assembly (14) and/or end effector (16) may be similarly used. As shown with respect to operation of ultrasonic surgical instrument (10), instrument actuator (36a) is more particularly a roll system actuator (36a) configured to rotate shaft assembly (14) about longitudinal axis (61). In contrast, instrument actuators (36b, 36c, 36d, 36e, 360 are linear system actuators (36b, 36c, 36d, 36e, 360 configured to translationally drive movement of portions of end effector (16) and/or shaft assembly (14) while simultaneously allowing for rotation of shaft assembly (14) via roll system actuator (36a).

Roll system actuator (36a) in one example includes a drive spool (96) rigidly connected to puck (38a) (see FIG. 2) and a driven spool (98) rigidly connected to proximal shaft portion (60) within housing (18). Drive spool (96) is mounted to rotate with puck (38a) (see FIG. 2) about a common puck axis, whereas driven spool (98) is mounted to rotate with proximal shaft portion (60) about the longitudinal axis (61). A cable (100) wraps around each of the drive and driven spools (96, 98), accommodating the differing orientation of the puck axis and longitudinal axis (61), such that rotating drive spool (96) via puck (38a) (see FIG. 2) urges rotation of driven spool (98). In turn, shaft assembly (14), including proximal and distal shaft portions (60, 62)

rotates about longitudinal axis (61) as indicated by arrow (66) (see FIG. 3A), such as by robotically driven actuation of puck (38a) (see FIG. 2).

Linear system actuators (36b, 36c, 36d, 36e, 360) of the present example include a gear-rack mechanism (102) having a rotatable drive gear (104), a translatable rack gear (106), and an idler gear (108) connected therebetween. Drive gears (104) are respectively connected to and rigidly project from pucks (38b, 38c, 38d, 38e, 380) (see FIG. 2), whereas each rack gear (106) is connected to another portion of proximal shaft portion (60) directing movement of shaft assembly (14) and/or end effector (16) as discussed above. Each rack gear (106) is cylindrical and rigidly connected relative to proximal shaft portion (60) to rotate therewith. Rack gear (106) is thereby configured to rotate with shaft assembly (14) while remaining meshed with idler gear (108). Rotating respective pucks (38b, 38c, 38d, 38e, 38f) (see FIG. 2) thus respectively rotates drive gears (104) and idler gears (108) to translate rack gears (106) as desired.

In the present example, with respect to FIGS. 2-4B and FIG. 6, linear system actuator (36b) has puck (38b) operatively connected to clamp arm (44) to direct movement of clamp arm (44) between the open and closed positions according to arrow (52). Linear system actuators (36c, 36d) have respective pucks (38c, 38d) operatively connected to clamp arm (44) to direct movement of clamp arm (44) around blade (46) in both the clockwise and counterclockwise directions according to arrow (53). In addition, linear system actuators (36e, 360) have respective pucks (38e, 380) operatively connected to articulation bands (74) to direct movement of articulation section (64) according to arrows (88, 90) for deflecting end effector (16) relative to longitudinal axis (61). Of course, in other examples, instrument actuators (36a, 36b, 36c, 36d, 36e, 360) may be alternatively configured with more or less actuators (36a, 36b, 36c, 36d, 36e, 360) and/or more or less movement as desired. The invention is thus not intended to be unnecessarily limited to instrument actuators (36a, 36b, 36c, 36d, 36e, 360) or particular movements of shaft assembly (14) and/or end effector (16) as described in the present example.

II. Exemplary Shift of Acoustic Drivetrain with Shaft Assembly Articulation

Figure 7A:
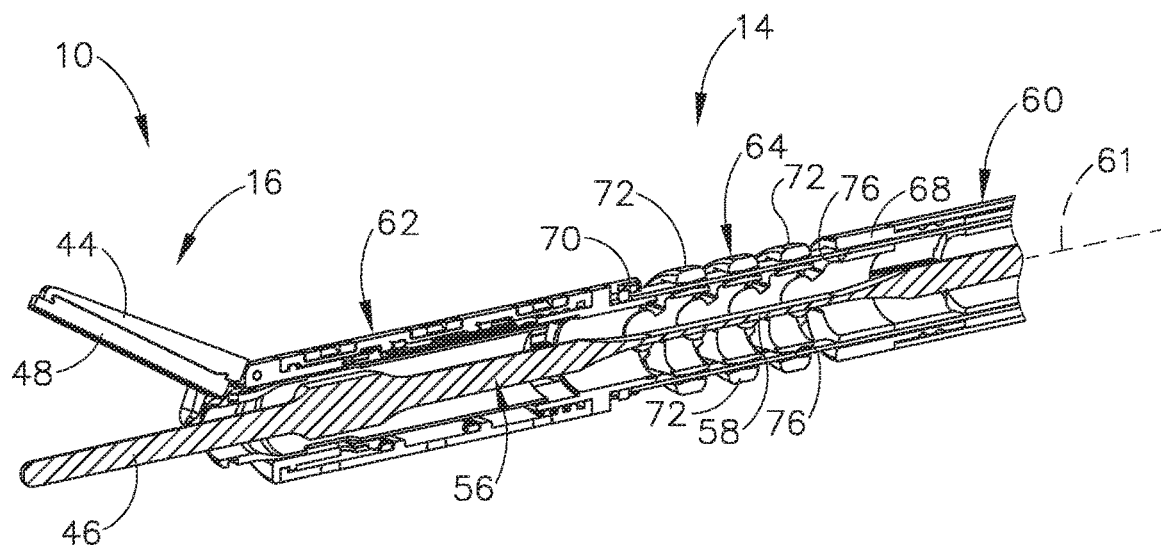
FIG. 7A depicts an enlarged, sectional, perspective view of the ultrasonic surgical instrument of FIG. 1 taken along a centerline thereof showing an ultrasonic blade of the end effector positioned relative to a clamp arm of the end effector with the shaft assembly in the straight configuration.
Figure 7B:
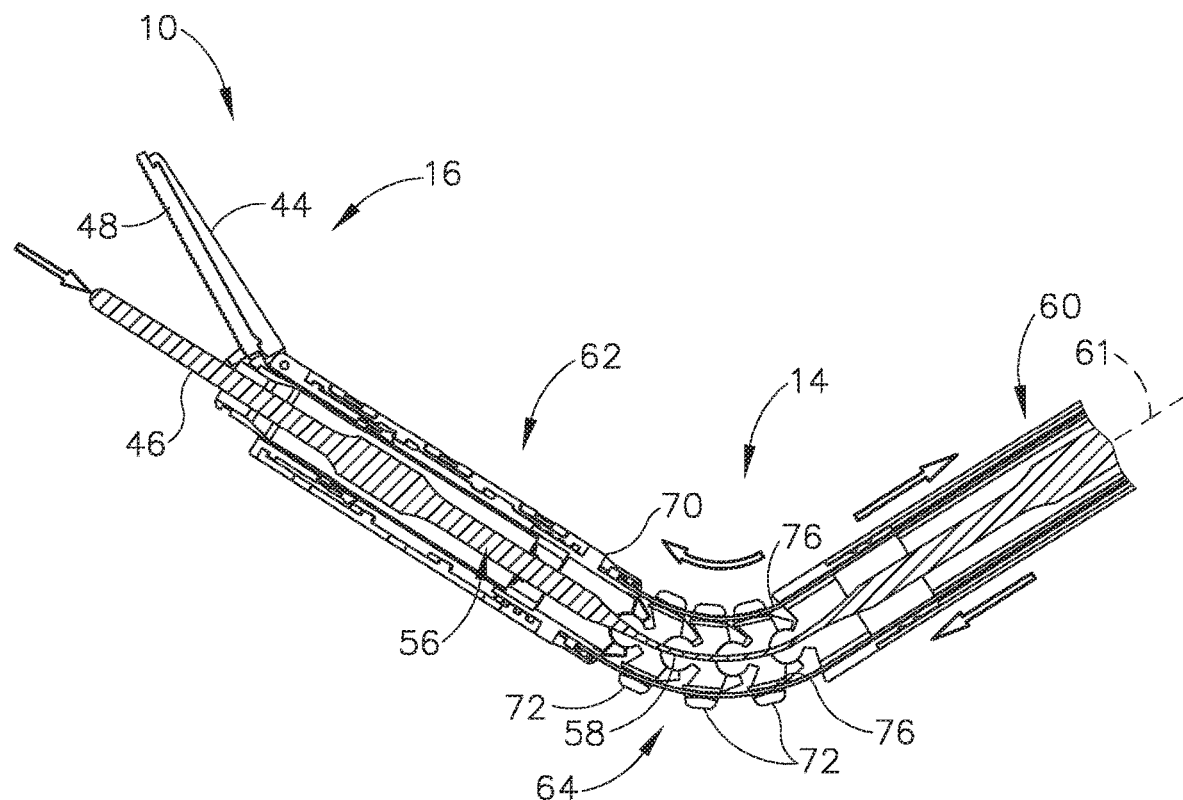
FIG. 7B depicts an enlarged, cross-sectional view of the ultrasonic surgical instrument of FIG. 7A taken along a centerline thereof showing the ultrasonic blade of the end effector positioned relative to the clamp arm of the end effector with the shaft assembly in the first articulated configuration.
Figure 8A:
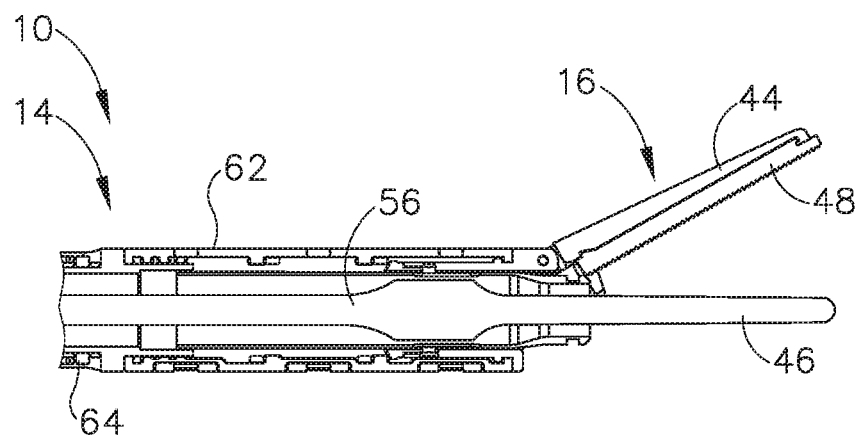
FIG. 8A depicts an enlarged, cross-sectional view of the end effector and the shaft assembly taken along a centerline thereof showing the ultrasonic blade positioned relative to the clamp arm with the shaft assembly in the straight configuration.
Figure 8B:
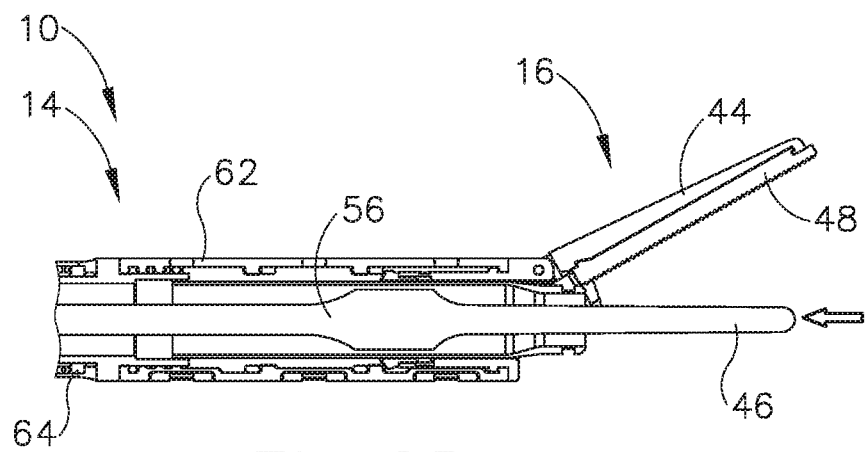
FIG. 8B depicts the enlarged, cross-sectional view of the end effector and the shaft assembly similar to FIG. 8A, but showing the ultrasonic blade positioned relative to the clamp arm with the shaft assembly in the first articulated configuration.

With respect to FIGS. 7A-8B, in one example, the distal tip of blade (46) is positioned to align in a predetermined alignment with a distal tip of clamp arm (44) in the straight configuration as shown in FIG. 7A and FIG. 8A. More particularly, such predetermined alignment positions the distal tip of blade (46) longitudinally flush with distal tip of clamp arm (44) in the closed position so that the distal tips of blade (46) and clamp arm (44) are positioned in a common plane perpendicular to an axis defined by blade (46). As articulation section (64) articulates from the straight configuration toward the articulated configuration as shown in FIG. 7B and FIG. 8B, articulation section (64) essentially elongates as the radius of curvature along articulation section (64) increases. In turn, blade (46) moves proximally relative to clamp arm (44) such that the distal tip of blade (46) and the distal tip of clamp arm (44) are no longer longitudinally aligned in the predetermined alignment due to a constant longitudinal length of acoustic waveguide (56) and blade (46) from transducer assembly (54) (see FIG. 6) to the distal tip of blade (46).

In some instances, it may be desirable to longitudinally adjust blade (46) relative to clamp arm (44) so as to maintain the predetermined alignment between blade (46) and clamp arm (44) with articulation section (64) in the straight and articulated configurations. Given the constant longitudinal length of acoustic waveguide (56) and blade (46), a proximal portion of the acoustic drivetrain, such as transducer assembly (54) (see FIG. 5), may be shifted in order to offset shift at a distal portion of the acoustic drivetrain, such as blade (46). To this end, a shiftable transducer assembly (254, 354) (see FIGS. 10A-11B) may be incorporated into ultrasonic surgical instrument (10) to align blade (46) with clamp arm (44) as desired, such as shown in FIG. 8A. In an alternative example shown in FIG. 9, an ultrasonic surgical instrument (210) has a pin (109) extending through a node of acoustic waveguide (56) and distal shaft portion (62) to fix acoustic waveguide (56) relative to distal shaft portion (62). In turn, pin (110) also longitudinally secures blade (46) in the predetermined alignment position relative to clamp arm (44). Still, the invention is not intended to be unnecessarily limited to mechanically fixing blade (46) relative to clamp arm (44). Moreover, such longitudinal adjustments of one or more portions of the acoustic drivetrain along longitudinal axis (61) (see FIG. 7B) may be performed in an alternative ultrasonic surgical instrument (not shown) without a clamp arm (not shown) or even to achieve other alignments relative to the acoustic drivetrain without regard for articulation of articulation section (64). The invention is thus not intended to be unnecessarily limited to use for maintaining the predetermined alignment between clamp arm (44) and blade (46) as shown and described herein. In any case, like numbers below indicate like features described above in greater detail.

A. Passively Shiftable Transducer Assembly

Figure 9:
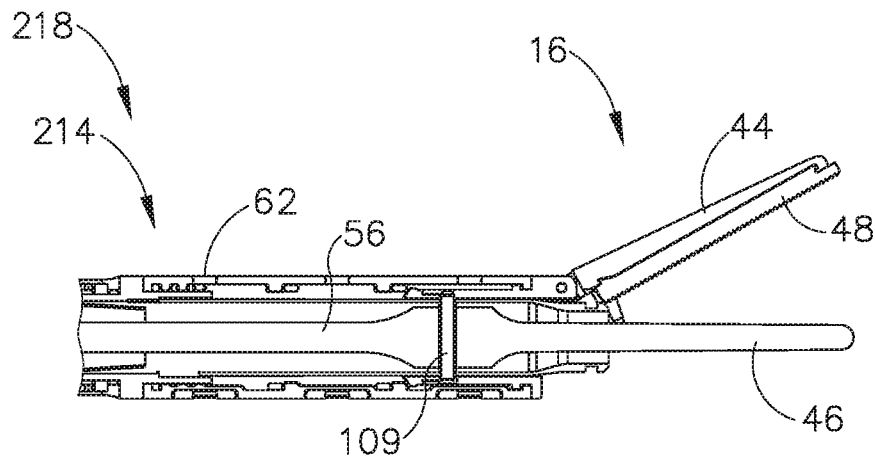
FIG. 9 depicts an enlarged, cross-sectional view of a second example of an ultrasonic surgical instrument taken along a centerline thereof with the end effector of FIG. 1 and a second exemplary shaft assembly having the ultrasonic blade fixed relative to the clamp arm in the straight configuration and the articulated configuration.
Figure 10A:
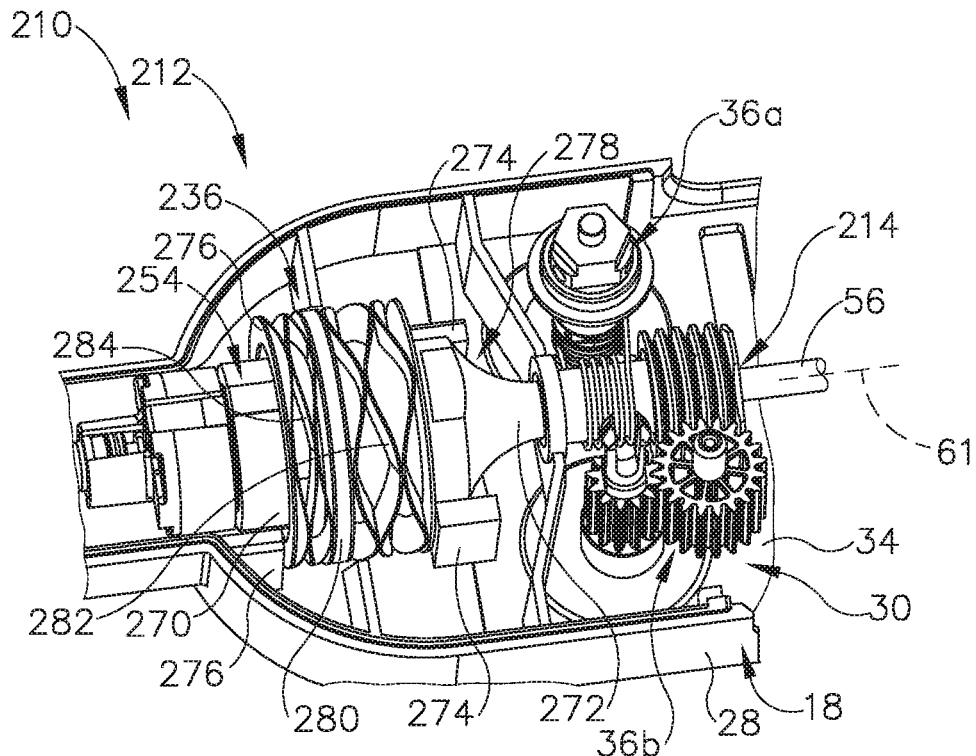
FIG. 10A depicts an enlarged, perspective view of a second exemplary base assembly of the ultrasonic surgical instrument of FIG. 9 having various components removed for greater clarity of a passively shiftable transducer assembly in a proximal position while the shaft assembly of FIG. 9 is in the straight configuration.
Figure 10B:
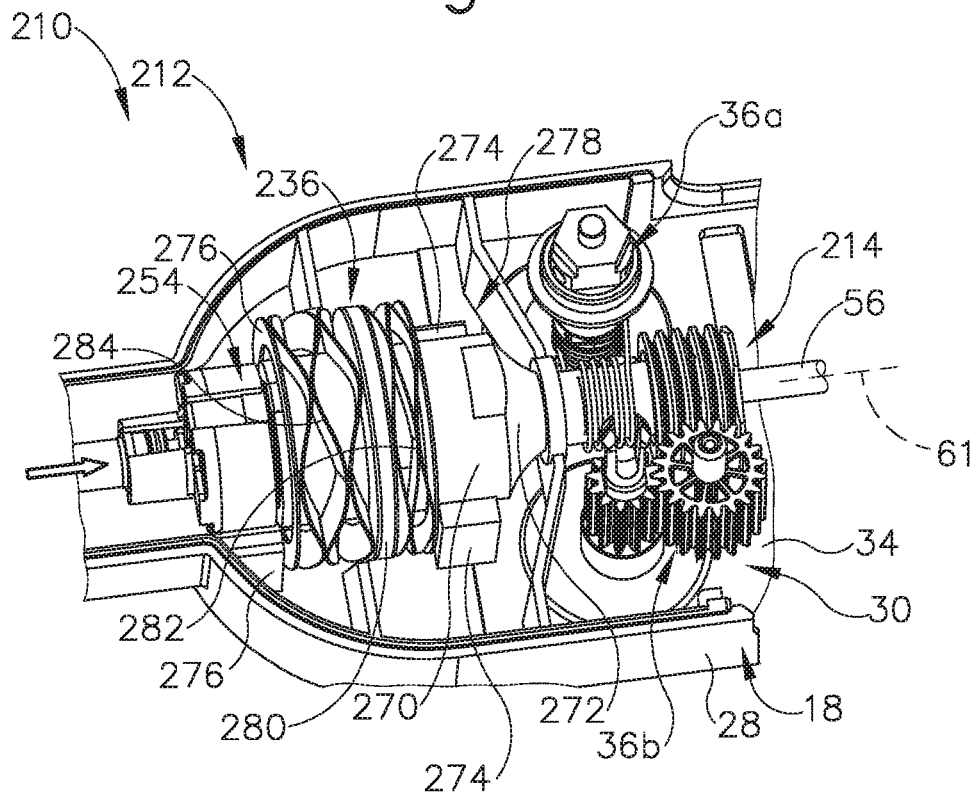
FIG. 10B depicts the enlarged, perspective view of the base assembly similar to FIG. 10A, but showing the passively shiftable transducer assembly in a distal position while the shaft assembly of FIG. 9 is in the articulated configuration.

FIGS. 9-10B show a second example of an ultrasonic surgical instrument (210) having end effector (16) and a second exemplary shaft assembly (214) with pin (109) through acoustic waveguide (56) such that blade (46) is longitudinally fixed in the predetermined alignment with clamp arm (44) as discussed above in greater detail. Ultrasonic surgical instrument (210) further includes a second exemplary base assembly (212) constructed similarly to base assembly (12) (see FIG. 6), but with a passively shiftable transducer assembly (254) and a passive system actuator (236). Shiftable transducer assembly (254) is movably coupled between housing (18) and passive system actuator (236) such that passive system actuator (236) enables shiftable transducer assembly (254) to be urged proximally or distally along longitudinal axis (61). Thereby, shiftable transducer assembly (254) accommodates longitudinal movement of acoustic waveguide (56) and blade (46) for maintaining the predetermined alignment. In the present example, pin (109) distally pulls on acoustic waveguide (56) when deflecting end effector away from longitudinal axis (61) such that shiftable transducer assembly (254) distally pulls shiftable transducer assembly (254) toward end effector (16) and along longitudinal axis (61). In contrast, pin (109) proximally pushes on acoustic waveguide (56) when deflecting end effector toward longitudinal axis (61) such that shiftable transducer assembly (254) proximally pushes shiftable transducer assembly (254) away from end effector (16) and along longitudinal axis (61). Shiftable transducer assembly (254) and system actuator (236) are thus referred to herein as "passive" given that shiftable transducer assembly (254) and system actuator (236) enable movement rather than providing initiating force for such movement. Although, as will be described below in greater detail, shiftable transducer assembly (254) and system actuator (236) may still provide force, such as a reactionary force, for maintaining tension and/or compression on acoustic waveguide (56).

Shiftable transducer assembly (254) of the present example shown in FIGS. 10A-10B more particularly includes a transducer housing (270) and a transducer horn (272) threaded into engagement with acoustic waveguide (56). Housing (18), in one example, has a pair of distal mount seats (274) and a pair of proximal mount seats (276) configured to longitudinally capture passive system actuator (236) while simultaneously allowing for longitudinal movement of transducer housing (270) and transducer horn (272) through a central space (278). Passive system actuator (236) thereby resiliently and translatably supports shiftable transducer assembly (254) relative to housing (18) along longitudinal axis (61), although it will be appreciated that the invention is not intended to be unnecessarily limited to resilient or translational mounting within housing (18).

More particularly, passive system actuator (236) of the present example includes an annular base seat (280) rigidly connected to and extending radially outward from transducer housing (270) as well as a distal annular spring (282) and a proximal annular spring (284). Distal annular spring (282) seats in compression between annular base seat (280) and distal mount seats (274) while proximal annular spring (284) seats in compression between annular base seat (280) and proximal mount seats (276). Distal and proximal mounts seats (274, 276) also laterally secure annular base seat (280) with transducer housing (270) on longitudinal axis (61). With respect to FIG. 10A, shiftable transducer assembly (254) is in a proximal position on longitudinal axis (61) while articulation section (64) (see FIG. 7A) is in a straight configuration (see FIG. 7A). In contrast, with respect to FIG. 10B, shiftable transducer assembly (254) is in a distal position on longitudinal axis (61) while articulation section (64) (see FIG. 7B) is in an articulated configuration (see FIG. 7B). In any longitudinal position between the distal and proximal positions, distal and proximal annular springs (282, 284) effectively balance force applied by pin (109) (see FIG. 9) while annular base seat (280) translatably supports transducer housing (270) relative to housing (18) of base assembly (212). As shown in the present example, distal and proximal annular springs (282, 284) are in compression. More particularly, compression of distal annular spring (282) increases while compression of proximal annular spring (284) decreases as shiftable transducer assembly (254) moves from the proximal position toward the distal position. Also, compression of distal annular spring (282) decreases while compression of proximal annular spring (284) increases as shiftable transducer assembly (254) moves from the distal position toward the proximal position.

Distal and proximal annular springs (282, 284) are configured to balance annular base seat (280) with transducer housing (270) supported therein according to a predetermined balance in any longitudinal position for accommodating movement of acoustic waveguide (56) resulting from articulation of articulation section (64) (see FIG. 7A). In one example, distal and proximal annular springs (282, 284) balance acoustic waveguide (56) in tension between the proximal and distal positions. In another example, distal and proximal annular springs (282, 284) balance acoustic waveguide (56) in compression between the proximal and distal positions. In still another example, distal and proximal annular springs (282, 284) balance acoustic waveguide (56) in compression toward the proximal position and in tension toward the distal position with a neutral, non-compression and non-tension state therebetween. In still yet another example, distal and proximal annular springs (282, 284) balance acoustic waveguide (56) in tension toward the proximal position and in compression toward the distal position with another neutral, non-compression and non-tension state therebetween. The invention is thus not intended to be unnecessarily limited to maintaining one or more portions of the acoustic drivetrain, such acoustic waveguide (56), in a particular state of compression or tension.

In use, with respect to FIGS. 6 and 9-10B, linear system actuators (36e, 36f) urge articulation bands (74) (see FIG. 7B) to direct movement of articulation section (64) for deflecting end effector (16) relative to longitudinal axis (61). Articulation section (64) articulates from the straight configuration toward the articulated configuration such that pin (84) distally pulls acoustic waveguide (56) with shiftable transducer assembly (254) from the proximal position toward the distal position to maintain the predetermined alignment between blade (46) and clamp arm (44). In this respect, movement of shiftable transducer assembly (254) is dependent upon articulation of articulation section (64). Annular base seat (280) of passive system actuator (236) supports transducer housing (270) and transducer horn (272) as shiftable transducer assembly (254) translates from the proximal position toward the distal position. In addition, annular base seat (280) compresses distal annular spring (282) against distal mount seats (274), while proximal annular spring (284) expands, distally urging annular base seat (280) toward distal mount seats (274). Distal and proximal annular springs (282, 284) continue to balance shiftable transducer assembly (254) and acoustic waveguide (56) with pin (109) as articulation section (64) is positioned in the articulated configuration during use. Thus, blade (46) remains in the same predetermined alignment with clamp arm (44) before, during, and after articulation of articulation section (64). Of course, any alignment may be desired, and the invention is not intended to be limited to the alignment of blade (46) shown and described in the present example. While the present example describes movement of articulation section (64) from the straight configuration toward the articulated configuration, it will be appreciated that shiftable transducer assembly (254) and associated components will move in opposite directions from those discussed above when moving articulation section (64) from the articulated configuration toward the straight configuration. Furthermore, in another example, articulation of articulation section (64) may be controlled by an operator via a handle assembly (not shown), such as by a knob (not shown) operatively connected to articulation section (64), rather than a robotic drive (not shown). The invention is thus not intended to be unnecessarily limited to use with base assembly (212) as shown and described herein.

B. Actively Shiftable Transducer Assembly

Figure 11A:
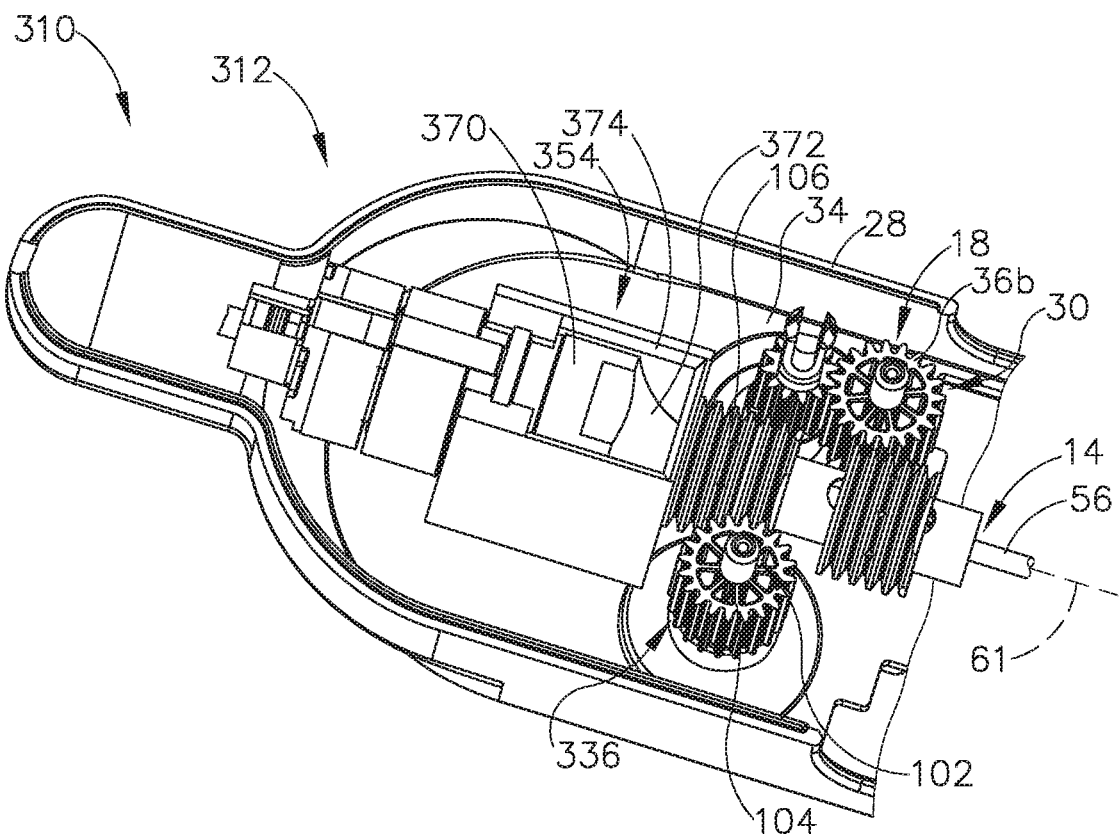
FIG. 11A depicts an enlarged perspective view of a third example of an ultrasonic surgical instrument with a third exemplary base assembly having various components removed for greater clarity of an actively shiftable transducer assembly in a proximal position.
Figure 11B:
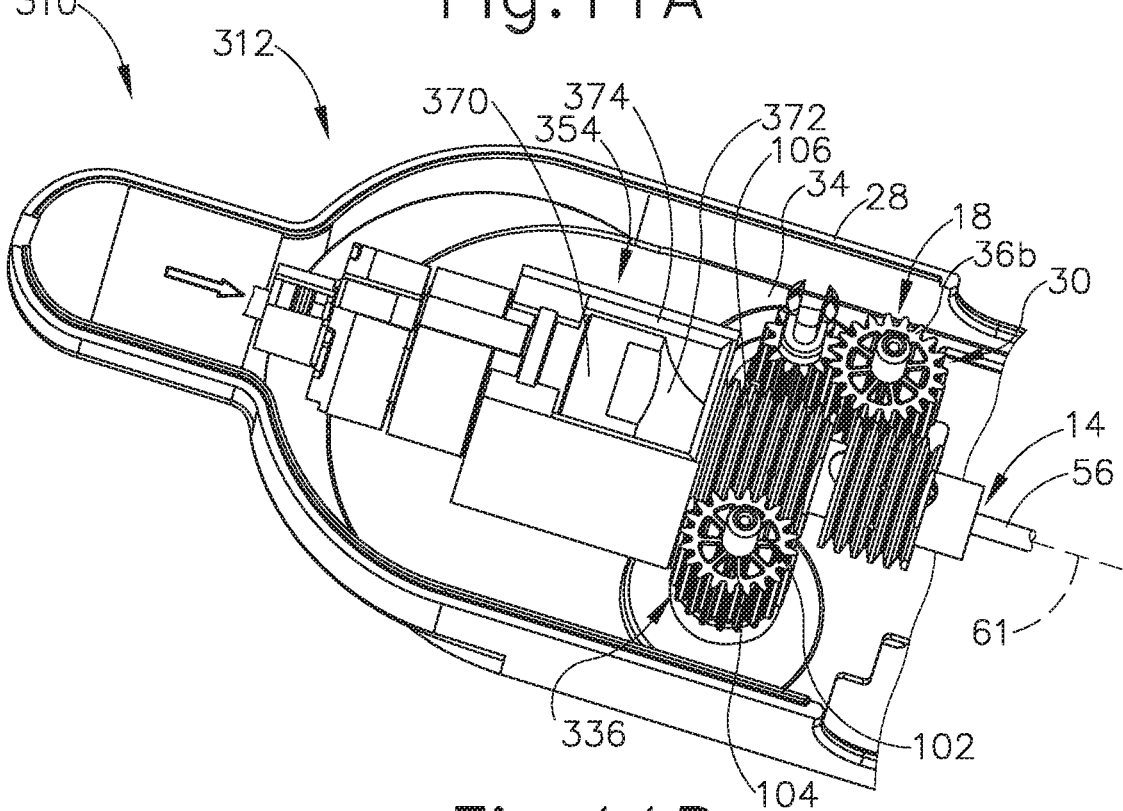
FIG. 11B depicts the enlarged, perspective view of the base assembly similar to FIG. 11A, but showing the actively shiftable transducer assembly in a distal position.

FIGS. 11A-11B show a third example of an ultrasonic surgical instrument (310) having end effector (16) (see FIG. 8A) and shaft assembly (14) without pin (109) (see FIG. 9) through acoustic waveguide (56) such that blade (46) may or may not be longitudinally maintained in the predetermined alignment with clamp arm (44). Ultrasonic surgical instrument (310) further includes a third exemplary base assembly (312) constructed similarly to base assembly (12) (see FIG. 6), but with an actively shiftable transducer assembly (354) and an active system actuator (336). Shiftable transducer assembly (354) is movably coupled between housing (18) and active system actuator (336) such that active system actuator (336) urges shiftable transducer assembly (354) proximally or distally along longitudinal axis (61). In one example, active system actuator (336) keys movement of shiftable transducer assembly (354) to accommodate longitudinal movement of acoustic waveguide (56) and blade (46)

(see FIG. 8A) for maintaining the predetermined alignment during articulation. Either shaft assembly (14) or shaft assembly (214) (see FIG. 9) may be incorporated into ultrasonic surgical instrument (310) in such an example. In another example, active system actuator (336) directs movement of shiftable transducer assembly (354) to position blade (46) in any longitudinal position relative to shaft assembly (14) and/or clamp arm (44) as desired by the operator. The invention is thus not intended to be unnecessarily limited to acoustic waveguide (56) being movable or fixed, such as via pin (109). Shiftable transducer assembly (354) and system actuator (336) are thus referred to herein as "active" given that shiftable transducer assembly (354) and system actuator (336) initiate movement by force rather than simply supporting such movement.

Shiftable transducer assembly (354) of the present example shown in FIGS. 11A-11B more particularly includes a transducer housing (370) and a transducer horn (372) threaded into engagement with acoustic waveguide (56). Active system actuator (336) of the present example includes gear-rack mechanism (102) with rotatable drive gear (104) and translatable rack gear (106) discussed above in greater detail as well as a transducer coupler (374) rigidly extending in the proximal direction from rack gear (106). Transducer coupler (374) receives transducer housing (370) to longitudinally secure transducer housing (370) and transducer horn (372) relative to rack gear (106) distally extending therefrom while laterally supporting transducer housing (370) and transducer horn (372). Rotatable drive gear (104) directly engages with rack gear (106) in the present example to selectively translate shiftable transducer assembly (354) as desired.

In use, with respect to FIGS. 8A and 11A-11B, drive gear (104) is selectively rotated via robotic drive (not shown) to linearly translate rack gear (106) along longitudinal axis (61) as desired. In turn, transducer coupler (374) urges shiftable transducer assembly (354) distally or proximally along longitudinal axis (61) thereby translating acoustic waveguide (56) and blade (46) as desired. In one example, active system actuator (336) keys movement of shiftable transducer assembly (354) to accommodate longitudinal movement of acoustic waveguide (56) and blade (46) for maintaining the predetermined alignment during articulation. Alternatively or in addition, active system actuator (336) directs movement of shiftable transducer assembly (354) to position blade (46) in any longitudinal position relative to shaft assembly (14) and/or clamp arm (44) as desired by the operator. In this respect, movement of shiftable transducer assembly (354) is independent upon articulation of articulation section (64) such that shiftable transducer assembly (354) may be moved with or without articulating articulation section (64). While articulation of articulation section (64) and/or shiftable transducer assembly (354) may be controlled by a robotic drive (not shown) as discussed in the present example, an operator may alternatively control articulation of articulation section (64) and/or shiftable transducer assembly (354) via a handle assembly (not shown), such as by a knob (not shown) operatively connected to articulation section (64) and/or shiftable transducer assembly (354). The invention is thus not intended to be unnecessarily limited to use with base assembly (312) as shown and described herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic surgical instrument, comprising: (a) an end effector including an ultrasonic blade; (b) a shaft assembly proximally extending from the end effector and defining a longitudinal axis, wherein the shaft assembly includes: (i) an articulation section configured to articulate from a straight configuration to an articulated configuration to thereby deflect the end effector relative to the longitudinal axis, and (ii) an acoustic waveguide having a flexible waveguide portion positioned within the articulation section and a distal waveguide portion acoustically connected to the ultrasonic blade; and (c) a body assembly proximally extending from the shaft assembly, including: (i) a housing, and (ii) a shiftable transducer assembly secured to the acoustic waveguide and configured to generate an ultrasonic energy, wherein the shiftable transducer assembly is movably mounted relative to the housing and configured to accommodate deflection of the end effector.

Example 2

The ultrasonic surgical instrument of Example 1, wherein the shiftable transducer assembly is further configured to move the acoustic waveguide relative to the shaft assembly while articulating the articulation section from the straight configuration to the articulated configuration.

Example 3

The ultrasonic surgical instrument of any one or more of Examples 1 through 2, wherein the end effector further includes a clamp arm movably connected relative to the ultrasonic blade in a predetermined longitudinal position, and wherein the shiftable transducer assembly is configured to move upon articulation of the articulation section to thereby move the acoustic waveguide relative to the articulation section and maintain the ultrasonic blade in the predetermined longitudinal position relative to the clamp arm.

Example 4

The ultrasonic surgical instrument of any one more of Examples 1 through 3, wherein the ultrasonic blade is fixed in the predetermined longitudinal position relative to the clamp arm.

Example 5

The ultrasonic surgical instrument of any one more of Examples 1 through 4, wherein the shaft assembly further includes a proximal shaft portion and a distal shaft portion, wherein the proximal shaft portion defines the longitudinal axis, and wherein the distal shaft portion supports the end effector distally extending therefrom.

Example 6

The ultrasonic surgical instrument of any one more of Examples 1 through 5, wherein the acoustic waveguide and the ultrasonic blade collectively define a constant longitudinal length.

Example 7

The ultrasonic surgical instrument of any one more of Examples 1 through 6, wherein the body assembly further includes an active system actuator connected to the shiftable transducer assembly and configured to selectively move the shiftable transducer assembly relative to the housing.

Example 8

The ultrasonic surgical instrument of Example 7, wherein the active system actuator is configured to selectively move the shiftable transducer assembly relative to the housing independent of articulation of the articulation section.

Example 9

The ultrasonic surgical instrument of any one more of Examples 7 through 8, wherein the active system actuator has a translatable rack gear secured relative to the shiftable transducer assembly, and wherein the translatable rack gear is configured to be selectively driven to thereby selectively translate the shiftable transducer assembly for translating the acoustic waveguide relative to the articulation section.

Example 10

The ultrasonic surgical instrument of any one more of Examples 1 through 6, wherein the body assembly further includes a passive system actuator connected to the shiftable transducer assembly and configured to enable movement of the shiftable transducer assembly relative to the housing.

Example 11

The ultrasonic surgical instrument of Example 10, wherein the passive system actuator is coupled between the shiftable transducer assembly and the housing and movably supports the shiftable transducer assembly such that the shiftable transducer assembly is configured to be urged with the acoustic waveguide for accommodating deflection of the end effector.

Example 12

The ultrasonic surgical instrument of any one more of Examples 10 through 11, wherein the shaft assembly further includes a proximal shaft portion and a distal shaft portion with the articulation section positioned therebetween, wherein the proximal shaft portion defines the longitudinal axis, and wherein the distal shaft portion supports the end effector distally extending therefrom, and wherein the acoustic waveguide has a distal waveguide end portion longitudinally fixed to the distal shaft portion such that articulating the articulation section translates the acoustic waveguide along the longitudinal axis to thereby urge movement of the shiftable transducer assembly.

Example 13

The ultrasonic surgical instrument of any one more of Examples 10 through 12, wherein the passive system actuator has a biasing element configured to resiliently bias the shiftable transducer assembly relative to the housing.

Example 14

The ultrasonic surgical instrument of any one more of Examples 10 through 13, wherein the shiftable transducer assembly is positioned on the longitudinal axis and resiliently biased along the longitudinal axis.

Example 15

The ultrasonic surgical instrument of any one more of Examples 1 through 14, wherein the body assembly further includes a robotic driven interface configured to connect to a robotic drive for robotically controlling articulation of the articulation section.

Example 16

An ultrasonic surgical instrument, comprising: (a) an end effector, including: (i) clamp arm configured to selectively move from an open position toward a closed position, and (ii) an ultrasonic blade longitudinally fixed relative to the clamp arm in a predetermined longitudinal position, (b) a shaft assembly proximally extending from the end effector, wherein the shaft assembly includes: (i) a proximal shaft portion defining a longitudinal axis, (ii) a distal shaft portion supporting the end effector distally extending therefrom, (iii) an articulation section positioned between the proximal and distal shaft portions, wherein the articulation section is configured to articulate from a straight configuration to an articulated configuration to thereby deflect the end effector relative to the longitudinal axis, (iv) an acoustic waveguide having a distal waveguide portion, a proximal waveguide portion and a flexible waveguide portion positioned therebetween within the articulation section, wherein the distal waveguide portion is acoustically connected to the ultrasonic blade; and (c) a body assembly proximally extending from the shaft assembly, including: (i) a shiftable transducer assembly secured to the proximal waveguide portion on the longitudinal axis and configured to generate an ultrasonic energy, (ii) a system actuator connected to the shiftable transducer assembly and configured to translate the shiftable transducer assembly along the longitudinal axis to maintain the predetermined longitudinal position of the ultrasonic blade relative to the clamp arm in the straight configuration and the articulated configuration.

Example 17

The ultrasonic surgical instrument of Example 16, wherein the acoustic waveguide and the ultrasonic blade define a constant longitudinal length in the straight configuration and the articulated configuration.

Example 18

The ultrasonic surgical instrument of any one more of Examples 16 through 17, wherein the body assembly further includes a robotic driven interface configured to connect to a robotic drive for robotically controlling articulation of the articulation section.

Example 19

The ultrasonic surgical instrument of any one more of Examples 16 through 18, wherein the shiftable transducer assembly is in a proximal position on the longitudinal axis while the articulation section is in the straight configuration, and wherein the shiftable transducer assembly is in a distal position on the longitudinal axis while the articulation section is in the articulated configuration.

Example 20

A method of deflecting an end effector of an ultrasonic surgical instrument, comprising: (a) moving a shiftable transducer assembly to longitudinally urge an acoustic waveguide relative to an articulation section of a shaft assembly of the ultrasonic surgical instrument; and (b) articulating the articulation section of the shaft assembly thereby deflecting the end effector relative to a longitudinal axis defined by the shaft assembly.

IV. Miscellaneous

Any one or more of the teaching, expressions, embodiments, examples, etc. described herein may be combined with any one or more of the teachings, expressions, embodiments, examples, etc. described in U.S. patent application Ser. No. 16/556,661, entitled "Ultrasonic Surgical Instrument with a Multi-Planar Articulating Shaft Assembly," filed on Aug. 30, 2019, published as U.S. Pub. No. 2021/0059709 on Mar. 4, 2021; U.S. patent application Ser. No. 16/556,625, entitled "Ultrasonic Surgical Instrument with Axisymmetric Clamping," filed on Aug. 30, 2019, published as U.S. Pub. No. 2021/0059707 on Mar. 4, 2021; U.S. patent application Ser. No. 16/556,635, entitled "Ultrasonic Blade and Clamp Arm Alignment Features," filed on Aug. 30, 2019, published as U.S. Pub. No. 2021/0059708 on Mar. 4, 2021; and/or U.S. patent application Ser. No. 16/556,727, entitled "Rotatable Linear Actuation Mechanism," filed on Aug. 30, 2019, published as U.S. Pub. No. 2021/0059711 on Mar. 4, 2021. The disclosure of each of these applications is incorporated by reference herein.

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. No. 8,623,027, issued Jan. 7, 2014; U.S. Pat. No. 9,023,071, issued May 5, 2015; U.S. Pat. No. 8,461,744, issued Jun. 11, 2013; U.S. Pat. No. 9,381,058, issued Jul. 5, 2016; U.S. Pub. No. 2012/0116265 now abandoned; U.S. Pat. No. 9,393,037, issued Jul. 19, 2016; U.S. Pat. No. 10,172,636, issued Jan. 8, 2019; and/or U.S. patent application Ser. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into another example of a robotic surgical system, and those of ordinary skill in the art will recognize that various teachings herein may be readily combined with various teachings of any of the following: U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No.

8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:
   (a) an end effector including an ultrasonic blade;
   (b) a shaft assembly proximally extending from the end effector and defining a longitudinal axis, wherein the shaft assembly includes:
      (i) an articulation section configured to articulate from a straight configuration to an articulated configuration to thereby deflect the end effector relative to the longitudinal axis, and
      (ii) an acoustic waveguide having a flexible waveguide portion positioned within the articulation section and a distal waveguide portion acoustically connected to the ultrasonic blade; and
   (c) a body assembly proximally extending from the shaft assembly, including:
      (i) a housing, and
      (ii) a shiftable transducer assembly secured to the acoustic waveguide and configured to generate an ultrasonic energy, wherein the shiftable transducer assembly is movably mounted relative to the housing and configured to accommodate deflection of the end effector,
   wherein the shiftable transducer assembly is further configured to move the acoustic waveguide relative to the shaft assembly while articulating the articulation section from the straight configuration to the articulated configuration.

2. The ultrasonic surgical instrument of claim 1, wherein the end effector further includes a clamp arm movably connected relative to the ultrasonic blade in a predetermined longitudinal position, and wherein the shiftable transducer assembly is configured to move upon articulation of the articulation section to thereby move the acoustic waveguide relative to the articulation section and maintain the ultrasonic blade in the predetermined longitudinal position relative to the clamp arm.

3. The ultrasonic surgical instrument of claim 2, wherein the ultrasonic blade is fixed in the predetermined longitudinal position relative to the clamp arm.

4. The ultrasonic surgical instrument of claim 1, wherein the shaft assembly further includes a proximal shaft portion and a distal shaft portion, wherein the proximal shaft portion defines the longitudinal axis, and wherein the distal shaft portion supports the end effector distally extending therefrom.

5. The ultrasonic surgical instrument of claim 1, wherein the acoustic waveguide and the ultrasonic blade collectively define a constant longitudinal length.

6. The ultrasonic surgical instrument of claim 1, wherein the body assembly further includes an active system actuator connected to the shiftable transducer assembly and configured to selectively move the shiftable transducer assembly relative to the housing.

7. The ultrasonic surgical instrument of claim 6, wherein the active system actuator is configured to selectively move the shiftable transducer assembly relative to the housing independent of articulation of the articulation section.

8. The ultrasonic surgical instrument of claim 6, wherein the active system actuator has a translatable rack gear secured relative to the shiftable transducer assembly, and wherein the translatable rack gear is configured to be selectively driven to thereby selectively translate the shiftable transducer assembly for translating the acoustic waveguide relative to the articulation section.

9. The ultrasonic surgical instrument of claim 1, wherein the body assembly further includes a passive system actuator connected to the shiftable transducer assembly and configured to enable movement of the shiftable transducer assembly relative to the housing.

10. The ultrasonic surgical instrument of claim 9, wherein the passive system actuator is coupled between the shiftable transducer assembly and the housing and movably supports the shiftable transducer assembly such that the shiftable transducer assembly is configured to be urged with the acoustic waveguide for accommodating deflection of the end effector.

11. The ultrasonic surgical instrument of claim 10, wherein the shaft assembly further includes a proximal shaft portion and a distal shaft portion with the articulation section positioned therebetween, wherein the proximal shaft portion defines the longitudinal axis, and wherein the distal shaft portion supports the end effector distally extending therefrom, and wherein the acoustic waveguide has a distal waveguide end portion longitudinally fixed to the distal shaft portion such that articulating the articulation section translates the acoustic waveguide along the longitudinal axis to thereby urge movement of the shiftable transducer assembly.

12. The ultrasonic surgical instrument of claim 10, wherein the passive system actuator has a biasing element configured to resiliently bias the shiftable transducer assembly relative to the housing.

13. The ultrasonic surgical instrument of claim 12, wherein the shiftable transducer assembly is positioned on the longitudinal axis and resiliently biased along the longitudinal axis.

14. The ultrasonic surgical instrument of claim 1, wherein the body assembly further includes a robotic driven interface configured to connect to a robotic drive for robotically controlling articulation of the articulation section.

15. An ultrasonic surgical instrument, comprising:
   (a) an end effector, including:
      (i) clamp arm configured to selectively move from an open position toward a closed position, and
      (ii) an ultrasonic blade longitudinally fixed relative to the clamp arm in a predetermined longitudinal position,
   (b) a shaft assembly proximally extending from the end effector, wherein the shaft assembly includes:
      (i) a proximal shaft portion defining a longitudinal axis,
      (ii) a distal shaft portion supporting the end effector distally extending therefrom,
      (iii) an articulation section positioned between the proximal and distal shaft portions, wherein the articulation section is configured to articulate from a straight configuration to an articulated configuration to thereby deflect the end effector relative to the longitudinal axis,
      (iv) an acoustic waveguide having a distal waveguide portion, a proximal waveguide portion and a flexible waveguide portion positioned therebetween within the articulation section, wherein the distal waveguide portion is acoustically connected to the ultrasonic blade; and
   (c) a body assembly proximally extending from the shaft assembly, including:
      (i) a shiftable transducer assembly secured to the proximal waveguide portion on the longitudinal axis and configured to generate an ultrasonic energy,
      (ii) a system actuator connected to the shiftable transducer assembly and configured to translate the shiftable transducer assembly along the longitudinal axis to maintain the predetermined longitudinal position of the ultrasonic blade relative to the clamp arm in the straight configuration and the articulated configuration,
      wherein the shiftable transducer assembly is in a proximal position on the longitudinal axis while the articulation section is in the straight configuration, and wherein the shiftable transducer assembly is in a distal position on the longitudinal axis while the articulation section is in the articulated configuration.

16. The ultrasonic surgical instrument of claim 15, wherein the acoustic waveguide and the ultrasonic blade define a constant longitudinal length in the straight configuration and the articulated configuration.

17. The ultrasonic surgical instrument of claim 15, wherein the body assembly further includes a robotic driven interface configured to connect to a robotic drive for robotically controlling articulation of the articulation section.

18. A method of deflecting an end effector of an ultrasonic surgical instrument, comprising:
   (a) moving a shiftable transducer assembly to longitudinally urge an acoustic waveguide relative to an articulation section of a shaft assembly of the ultrasonic surgical instrument; and
   (b) articulating the articulation section of the shaft assembly thereby deflecting the end effector relative to a longitudinal axis defined by the shaft assembly.

\* \* \* \* \*